United States Patent [19]

Seth et al.

[11] Patent Number: 5,104,656

[45] Date of Patent: Apr. 14, 1992

[54] PERCUTANEOUS TREATMENT WITH A HIGH POTENCY NON-STEROIDAL ANTI-INFLAMMATORY AGENT

[76] Inventors: Pyare L. Seth, Ischuppacherweg-4, 4147 Pfeffingen/BL, Switzerland; Lorne A. Campbell, 6727 Quartzite Canyon Pl., Tucson, Ariz. 85718

[21] Appl. No.: 356,429

[22] Filed: Jun. 16, 1989

[51] Int. Cl.$^5$ ............................................. A61K 9/10
[52] U.S. Cl. .................................. 424/401; 514/887; 514/941; 514/943; 514/947
[58] Field of Search ................. 424/401; 514/784, 887, 514/938, 941, 943, 947

[56] References Cited

U.S. PATENT DOCUMENTS

| | | | |
|---|---|---|---|
| 4,360,518 | 11/1982 | Rovee et al. | 514/887 |
| 4,555,524 | 11/1985 | Gruber et al. | 514/947 |
| 4,647,586 | 3/1987 | Mizushima et al. | 514/938 |
| 4,720,353 | 1/1988 | Bell | 514/887 |
| 4,746,675 | 5/1988 | Makino et al. | 514/947 |
| 4,849,418 | 7/1989 | Löhner et al. | 514/947 |
| 4,873,081 | 10/1989 | Ogiso | 514/947 |

*Primary Examiner*—Thurman K. Page
*Assistant Examiner*—A. Hulina
*Attorney, Agent, or Firm*—Vincent L. Carney

[57] ABSTRACT

To prepare an analgesic, anti-inflammatory cream, ibuprofen-S is dissolved in the PEG-7-glycerylcocoate and propylene glycol by slightly warming the solution to about 40 degrees Centigrade. Fractionated coconut oil, di-isopropyladipate, stearic acid, cetyl alcohol, polyoxyl-40-stearate, sorbitan-monostearate and propylparaben are mixed and heated to 70 degrees Centigrade. Methylparaben Sod. is dissolved in demineralized water and heated to 70 degrees Centigrade. The above oil and water phase components are mixed together, cooled to about 50 degrees Centigrade and the ibuprofen-S solution is added to the emulsion. The emulsion is homogenized and cooled to room temperature to form the cream.

2 Claims, No Drawings

PERCUTANEOUS TREATMENT WITH A HIGH POTENCY NON-STEROIDAL ANTI-INFLAMMATORY AGENT

BACKGROUND OF THE INVENTION

This invention relates to anti-inflammatory agents and methods of preparing and using anti-inflammatory preparations.

Anti-inflammatory and analgesic agents have been topically applied. In one prior art example (European Patent Application, EP0087062B1, 09, 02, 83), the preparation and use of an emulsion cream containing a maximum of 5 percent ibuprofen in its racemic form is described. The patent application claims that since ibuprofen is a highly lipophilic drug and has a very poor aqueous solubility, it was not possible to disperse ibuprofen in an aqueous phase to make a suitable cream. Accordingly, the ibuprofen cream was prepared by dissolving it in the lipid phase using the oily components of the formula and then emulsifying the same as an o/w emulsion cream. However, it is known that a lipophilic drug dissolved in a lipid phase of the emulsion system has poor release properties and hence will show a very poor cutaneous absorption at the site of application. Surprisingly, it was found that ibuprofen in its racemic form as well as in its enantiomeric S-form, both of which have very lipophilic properties, can be easily dissolved in very high concentrations in certain hydrophilic solvents. These hydrophilic solvents such as PEG-7-glycerylcocoate or PEG-200 monolaurate are miscible with both aqueous or hydrophilic as well as the lipid components and thus do not suffer from the disadvantage of the poor release properties associated with the emulsion systems where lipophilic drugs are dissolved in lipids. Additionally, these solvents act as very good cutaneous absorption promoters in the intact skin. The skin penetration properties are further enhanced when combined with hydrophilic excipients such as propylene glycol. Hence, the objective of the present invention was to develop a high concentration ibuprofen containing emulsion cream that contains ibuprofen or its S-enantimoer dissolved in the hydrophilic phase of the emulsion cream that also enhances skin penetrability.

SUMMARY OF THE INVENTION

Accordingly, it is an object of the invention to provide a novel formulation of ibuprofen in its racemic and enantiomeric-S form for topical application.

It is a still further object of the invention to provide a novel treatment for certain disorders alleviated with ibuprofen.

It is a still further object of the invention to provide a novel formulation of ibuprofen which provides better percutaneous penetration of ibuprofen.

It is a still further object of the invention to provide novel treatment of certain disorders requiring analgesic, antipyretic and/or anti-antipyretic inflammatory remedies.

In accordance with the above and further objects of the invention, an oil in water emulsion cream containing high concentration of ibuprofen-S is prepared. This cream is applied to the skin for enhanced percutaneous penetration of the ibuprofen-S.

The cream includes ibuprofen-S in a range of between 1 and 10 percent by weight, a hydrophilic solvent and a hydrophilic co-solvent for the ibuprofen-S, which also act as a penetration enhancer.

To use ibuprofen as a general analgesic and anti-inflammatory agent without causing gastrointestinal difficulties in some persons, the preparation is applied to the skin at suitable sensitive points in sufficient quantities to serve the purpose as a general analgesic and anti-inflammatory agent. The cream is applied to the skin in volumes of 1 cubic centimeter to 10 cubic centimeters or 1 gram to 5 grams of weight.

In a preferred method of forming the cream, the ibuprofen-S is first dissolved in hydrophilic solvent. The oily components together with surfactants of the formula are mixed with the aqueous phase to form an emulsion and then the ibuprofen-S solution is mixed into the emulsion and the combination cooled to form a cream. The cream is applied to the area to be treated so as to provide better anti-inflammatory and analgesic effects than the prior art topical preparations.

DETAILED DESCRIPTION

Broadly, a relatively high concentration of 1 to 10 percent ibuprofen-S contained in a cream with penetration enhancers is rubbed on the skin in sufficient doses to provide general analgesic effects, general anti-inflammatory effects and general antipyretic effects. Ibuprofen-S may be obtained from Sepracor, Inc., 33 Locke Drive, Marlborough, MA 01752.

The cream is formed from dissolving ibuprofen-S in hydrophilic solvents; mixing the oil phase and surfactants of the formula with aqueous phase together to form an emulsion and then adding the solution of ibuprofen-S contained in hydrophilic solvent and homogenizing together.

The preferred dosage is applied by rubbing the cream into the skin over the painful or inflamed area as needed. Generally, this requires 1.00 to 5.00 grams of cream for about a 10 square centimeter area.

A more specific formulation includes: (1) an oily component of oil/water emulsion such as fractionated coconut oil in the range of 2 to 15 percent and preferably 10 percent; (2) di-isopropyladipate in the range of 1 to 10 percent and preferably 5 percent; (3) a hydrophilic solvent for the hydrophobic drug (ibuprofen-S) which also acts as a penetration enhancer such as PEG.-7-glycerylcocoate in the range of 1 to 10 percent and preferably 5 percent; (4) consistency forming components and auxiliary emulsifiers such as stearic acid in the range of 1 to 10 percent and preferably 5 percent; (5) cetyl alcohol in the range of 1 to 5 percent and preferably 5 percent; (6) a hydrophilic surfactant such as polyoxyl-40 stearate in the range of 1 to 10 percent and preferably 2.5 percent; (7) a hydrophobic surfactant such as sorbitan-monostearate in the range of 1 to 5 percent and preferably 2.5 percent; (8) ibuprofen-S in the range of 1 to 10 percent and preferably 10 percent; (9) a hydrophilic co-solvent for the drug, humectant and a penetration enhancer such as propylene glycol in the range of 1 to 10 percent and preferably 2.5 percent; (10) a preservative such a propylparaben in the range of 0.05 to 0.1 percent and preferably 0.05 percent; (11) a preservative such as methylparaban in the range of 0.15 to 0.3 percent and preferably 0.15 percent; and (12) demineralized water for the aqueous phase of about 62.3 percent.

Although a specific formulation and effective ranges based on present knowledge of the art of the compound and limited experiments are given above, there are many equivalents known in the art for some of the ingredients. For example, instead of fractionated coconut oil, any other plant, mineral or semi-synthetic oil may be used; instead of di-isopropyladipate, isopropylmyristate or isopropylpalmitate may be used; instead of PEG.-7-glycerylococoate, PEG-(200-400) laurate (such as mono or diesters) may be used; instead of polyoxyl 40 stearate, any other suitable hydrophilic and hydrophobic surfactants may be used; and instead of propylene glycol, PEG-400 may be used.

The surprising advantage of this formulation is that ibuprofen-S solution in Cetrol HE (Trademark for PEG-7-glycerylcocoate) (with or without propylene glycol) can be mixed with either the lipid or aqueous phase before emulsifying the cream or after their emulsification and thus it can be added into any standard o/w or w/o cream base and has a universal possibility of being incorporated into practically every emulsion system devised.

To form the preparation, the ibuprofen-S is first dissolved in the hydrophilic solvent. The oil components together with surfactants are mixed with demineralized water to form an emulsion and the the dissolved ibuprofen in the hydrophilic solvents are mixed into the emulsion and homogenized together at a temperature of at least 40 degrees Centigrade. The emulsion is then cooled to form a cream for use.

More specifically, ibuprofen-S is dissolved in the given amount of PEG-7-glycerylcocoate and propylene glycol (solvent and co-solvents) by slightly warming the solution to about 40 degrees Centigrade. Next, the fractionated coconut oil, di-isopropyladipate, stearic acid, cetyl alcohol, polyoxyl-40-stearate, sorbitan-monostearate and propylparaben are mixed and heated to 70 degrees Centigrade, forming a clear solution of oily components. The methylparaben is dissolved in demineralized water and heated to 70 degrees Centigrade to form the water phase of the emulsion.

The oil and water phase components are slowly mixed with rapid stirring, using an ultra stirrer. While continuing the stirring, the emulsion is cooled to about 50 degrees Centigrade and then the ibuprofen-S solution is added to the oil-water emulsion and the emulsion is homogenized. It is slowly cooled to room temperature to form a cream.

The invention is illustrated by the following examples:

EXAMPLES

Example 1

Ten percent weight of ibuprofen-S is dissolved in 5 percent weight of PEG-7-glycerylcocoate and 2.5 percent weight of propylene glycol (solvent and co-solvents) by slightly warming the solution to about 40 degrees Centigrade.

The following components of the lipid phase and surfactants are mixed in the following percentages by weight/weight (with respect to the final product) and heated to about 70 degrees Centigrade to form a clear solution:

| | |
|---|---|
| Fractionated coconut oil | 10.0 |
| Di-isopropyladipate | 5.0 |
| Stearic acid | 5.0 |
| Cetyl alcohol | 5.0 |
| Polyoxyl-40-stearate | 2.5 |
| Sorbitan-monostearate | 2.5 |

-continued

| | |
|---|---|
| Propylparaben | 0.05 |

Methylparaben is dissolved in demineralized water and heated to 70 degrees Centigrade to form the aqueous phase. With rapid stirring, using an ultra stirrer, the aqueous phase is added to the lipid phase while the stirring is continued, the emulsion is cooled to about 50 degrees Centigrade and then the ibuprofen-S solution is added to the oil-water emulsion formed earlier. The final mixture is homogenized and then slowly cooled to room temperature to form a cream.

The cream is spread onto a sore portion of the body with one application every 6 hours. This treatment relieves the soreness shortly after the first application.

Example 2

The composition may also be made by dissolving 10 percent ibuprofen-S in 7.5 percent PEG-(200-monolaurate) by slightly warming the solution to about 40 degrees Centigrade.

In this example, the following components of the oily phase are mixed in the following percentages by weight/weight (with respect to the final product) and heated to about 70 degrees Centigrade to form a clear solution:

| | |
|---|---|
| Fractionated coconut oil | 10.0 |
| Isopropylmyristate | 5.0 |
| Stearic acid | 5.0 |
| Cetyl Alcohol | 5.0 |
| Polyoxyl-40-stearate | 2.5 |
| Sorbitan-monostearate | 2.5 |
| Propylparaben | 0.05 |

Methylparaben is dissolved in demineralized water and heated to 70 degrees Centigrade to form the water component. With rapid stirring, using an ultra stirrer, the water component is added to the oil component. While the stirring is continued, the emulsion is cooled to about 50 degrees Centigrade and then the ibuprofen-S solution is added to the oil-water emulsion formed earlier. The final mixture is homogenized and then slowly cooled to room temperature to form a cream.

Example 3

Take 10.0 grams of ibuprofen-S and dissolve it by slightly warming to approximately 40 degrees Centigrade in a mixture of 5.0 grams Cetrol (Trademark for PEG-7-glycerylcocoate) and 2.5 grams Propylene Glycol (solution A).

Separately take 10 grams of Cetomacrogol Emulsifying Wax BL-1988 (Trademark for polyethylene glycol 1000 monoacetyl ether) and melt it by heating to 70 degrees Centigrade together with 5.0 grams of Miglyo1892 (Trademark for mixture of polyoxyl stearate and cetyl alcohol) and 5.0 grams of isopropylmyristate (solution B).

Heat 62 grams of demineralized water to 60 degrees Centigrade. With rapid stirring, add into it slowly the heated oil emulgator (solution B), to form an emulsion. Into this emulsion, add with continued stirring the ibuprofen-S (solution A). Cool slowly and if necessary, add necessary amounts of water to give a final weight of 200 grams of the ibuprofen cream. Stir gently until cooled to room temperature.

The topical preparation of this invention has the advantages of providing a greater concentration of ibuprofen-S to the area covered so as to provide better anti-inflammatory and analygesic effects than prior art topical preparations.

Although a preferred embodiment has been described with some particularity, many modifications and variations may be made in the preferred embodiment without deviating from the invention. Accordingly, it is to be understood that, within the scope of the appended claims, the invention may be practiced other than as specifically described.

What is claimed is:

1. A method of making an analgesic, anti-inflammatory cream, comprising the steps of:

dissolving at least 1 percent ibuprofen-S w/w of the cream in PEG-7-glycerylcocoate and propylene glycol by slightly warming the solution to about 40 degrees Centigrade;

mixing fractionated coconut oil, di-isopropyladipate, stearic acid, cetyl alcohol, polyoxyl-40-stearate, sorbitan-monostearate and propylparaben and heating to 70 degrees Centigrade wherein a clear solution of oily components is formed;

dissolving methylparaben in demineralized water and heating it to 70 degrees Centigrade to form the water phase of the emulsion;

slowly mixing and homogenizing the oil and water phase components together by adding the water components to the oil components and stirring rapidly;

cooling the emulsion to about 50 degrees Centigrade, while continuing the stirring;

adding the ibuprofen-S solution to the oil-water emulsion;

homogenizing the emulsion; and slowly cooling the emulsion to room temperature to form a cream.

2. A method of making an analgesic, anti-inflammatory cream according to claim 1, wherein:

ibuprofen-S in the range of 1 to 10 percent w/w of the cream is dissolved in PEG-7-glycerylcocoate in the range of 1 to 10 percent w/w of the cream and propylene glycol in the range of 1 to 10 percent w/w of the cream by slightly warming the solution to about 40 degrees Centigrade;

fractionated coconut oil is in the range of 2 to 15 percent w/w of the cream, di-isopropyladipate in the range of 1 to 10 percent w/w of the cream, stearic acid in the range of 1 to 10 percent w/w of the cream, cetyl alcohol in the range of 1 to 5 percent w/w of the cream, polyoxyl-40-stearate in the range of 1 to 10 percent w/w of the cream, sorbitan-monostearate in the range of 1 to 5 percent w/w of the cream and propylparaben in the range of 0.05 to 0.1 percent w/w of the cream are mixed and heated to 70 degrees Centigrade wherein a clear solution of oily components are formed; and methylparaben in the range of 0.15 to 0.3 percent w/w of the cream is dissolved in about 62.3 percent w/w of the cream demineralized water and heating it to 70 degrees Centigrade to form the water phase of the emulsion.

* * * * *